United States Patent
Haarmann et al.

(10) Patent No.: US 8,349,552 B2
(45) Date of Patent: *Jan. 8, 2013

(54) FABRICATING A FLEXIBLE RAPID BLOOD COOLING SYSTEM

(75) Inventors: Klaus H. Haarmann, Frisco, TX (US); Anthony Alleva, Keansburg, NJ (US); Thomas-Laurent Bingas, Skaneateles, NY (US)

(73) Assignee: TCP Reliable, Inc., Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/431,383

(22) Filed: Mar. 27, 2012

(65) Prior Publication Data

US 2012/0266564 A1  Oct. 25, 2012

Related U.S. Application Data

(60) Provisional application No. 61/477,796, filed on Apr. 21, 2011.

(51) Int. Cl.
*A01D 22/00* (2006.01)
*F28D 15/00* (2006.01)
*B29D 22/00* (2006.01)
*B29D 23/00* (2006.01)

(52) U.S. Cl. ............ 435/2; 428/34.1; 428/35.7; 428/69; 428/72; 428/76; 165/46; 165/104.11; 165/104.19; 165/104.21; 220/560.13; 220/592.01; 252/71; 252/73; 62/458; 62/457.9

(58) Field of Classification Search ........................ None
See application file for complete search history.

(56) References Cited

U.S. PATENT DOCUMENTS

| | | | |
|---|---|---|---|
| 4,938,758 A * | 7/1990 | Al-Sioufi | ...................... 604/410 |
| 5,899,088 A | 5/1999 | Purdum | |
| 6,482,332 B1 | 11/2002 | Malach | |
| 6,645,598 B2 * | 11/2003 | Alderman | ...................... 428/69 |
| 2004/0202783 A1 | 10/2004 | Baumann et al. | |
| 2006/0112717 A1 | 6/2006 | Walton | |

(Continued)

FOREIGN PATENT DOCUMENTS

EP  1053726 B1  11/2000

(Continued)

OTHER PUBLICATIONS van der Meer et al. (Overnight storage of whole blood: a comparison of two designs of butane-1,4-diol cooling plates; 2007, Transfusion, vol. 47, pp. 2048-2053).*

*Primary Examiner* — Sharmila G. Landau
*Assistant Examiner* — Shannon Janssen
(74) *Attorney, Agent, or Firm* — Eric P. Mirabel

(57) ABSTRACT

A new blood unit cooling system was designed to cool blood rapidly to about 22° C. and maintain it at about that temperature, even in ambient temperature extremes, for several hours. The system incorporating a preferred eutectic solution including 98% 1-dodecanol, 1.5% myristyl alcohol and 0.5% 1-decanol (having, a melting point of about 23° C.) contained in a sealed flexible polymer layer, was used to cool whole blood-filled bags. The preferred design uses inner and outer containers, each made of transparent polyethylene sheets, where the inner compartments are filled with the solution and sealed, and then placed into each compartment in an outer container, wherein two compartments in the outer container are separated by a flattened and sealed portion of the polyethylene.

9 Claims, 10 Drawing Sheets

U.S. PATENT DOCUMENTS

| | | |
|---|---|---|
| 2006/0233986 A1* | 10/2006 | Gutsche et al. ............. 428/35.2 |
| 2007/0125483 A1 | 6/2007 | Barnett et al. |
| 2008/0057574 A1 | 3/2008 | Romero |
| 2009/0297810 A1 | 12/2009 | Fiscus et al. |
| 2010/0010599 A1* | 1/2010 | Chen et al. .................... 607/112 |

FOREIGN PATENT DOCUMENTS

| | | |
|---|---|---|
| WO | WO2011077268 A1 | 6/2011 |

* cited by examiner

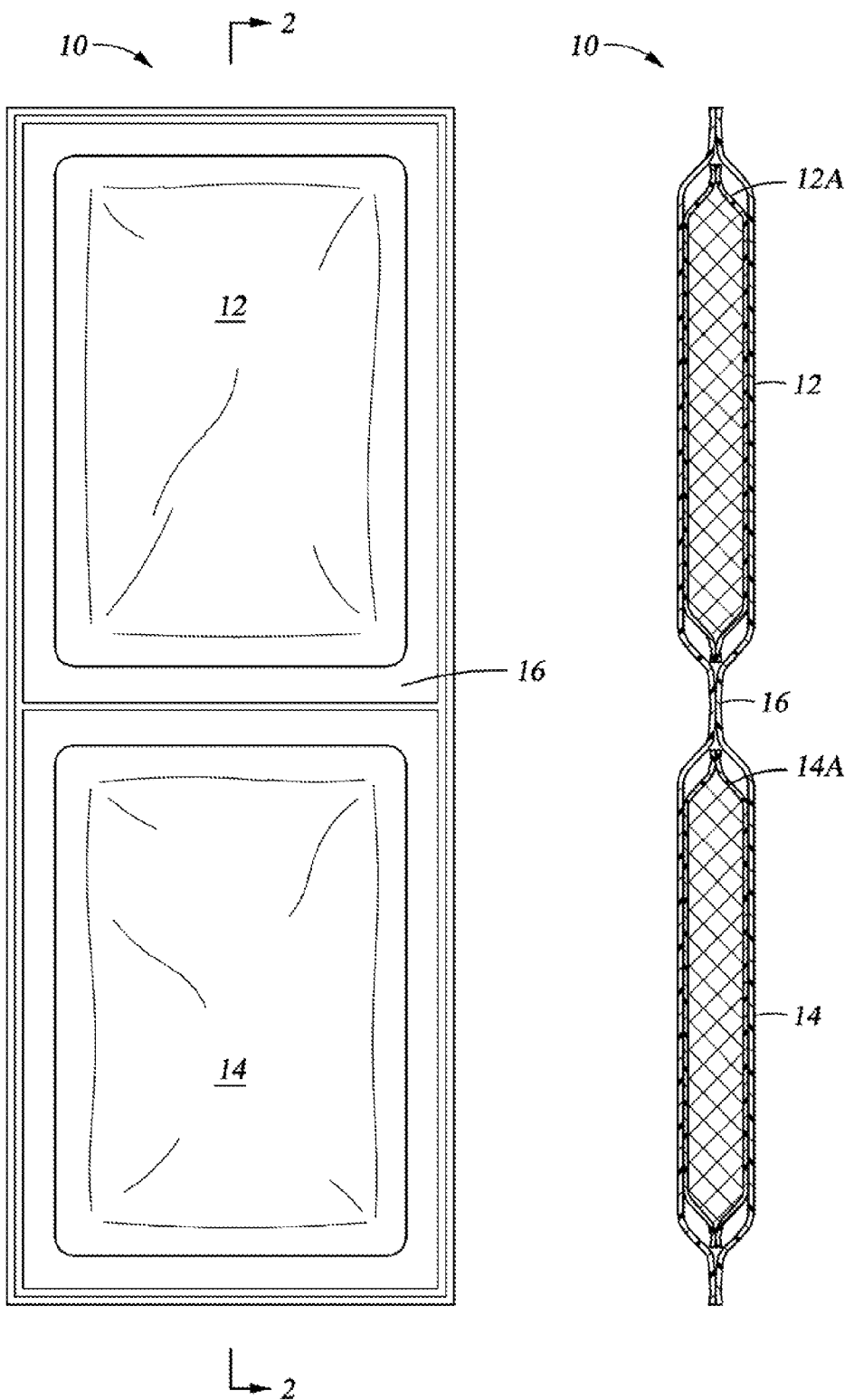

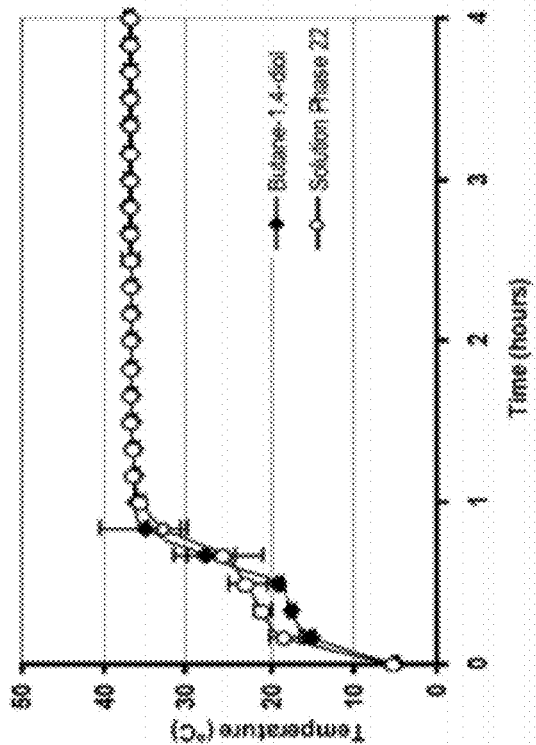
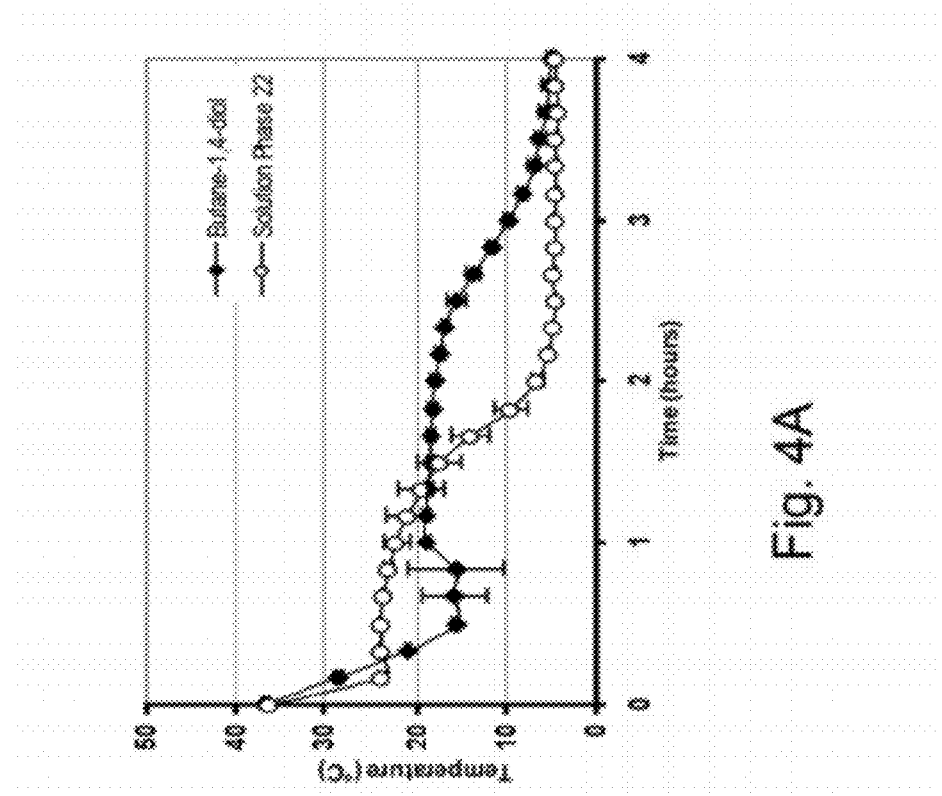
Fig. 4B
Fig. 4A

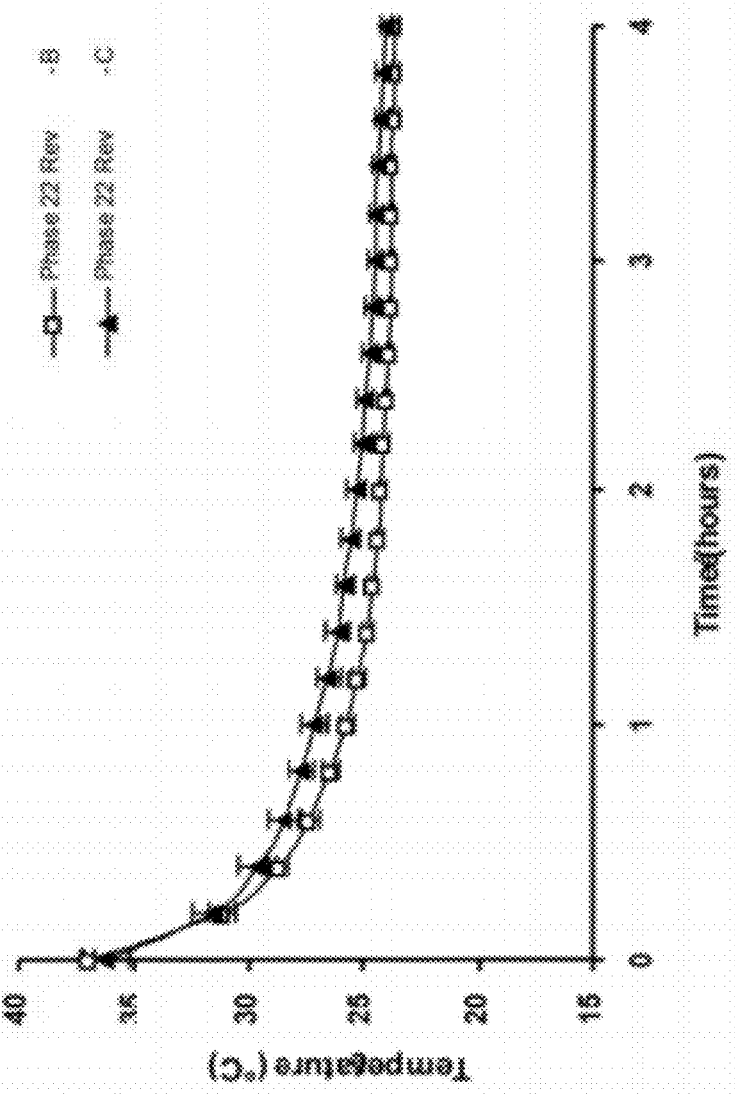
Fig. 5 – Kinetics of Cooling to 22 ± 2°C of 25% Glycerol Pouches Pre-Equilibrated at 37 ± 2°C Using Preferred Embodiment ("Phase 22 Rev B'") and another embodiment*

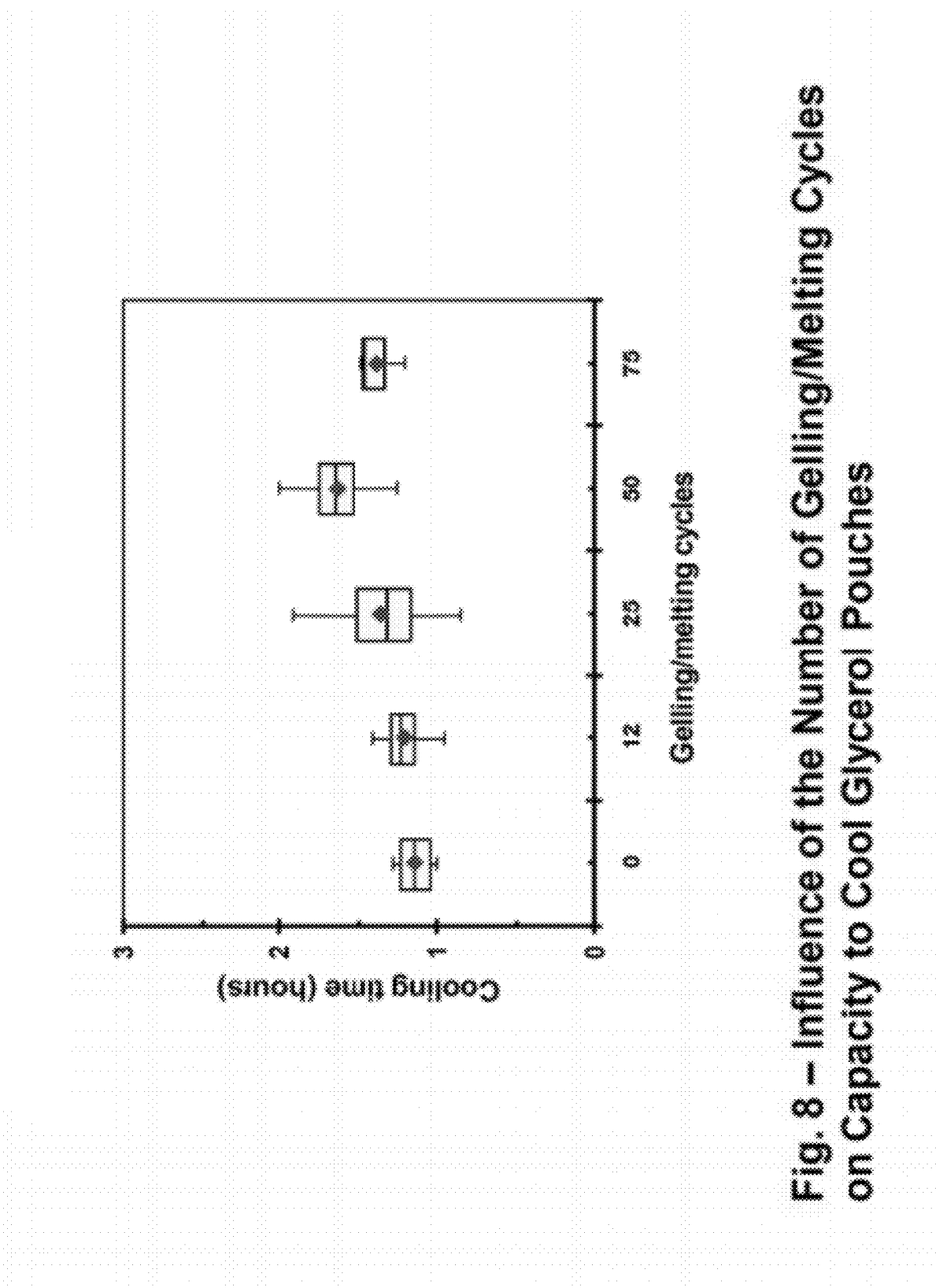
Fig. 8 – Influence of the Number of Gelling/Melting Cycles on Capacity to Cool Glycerol Pouches

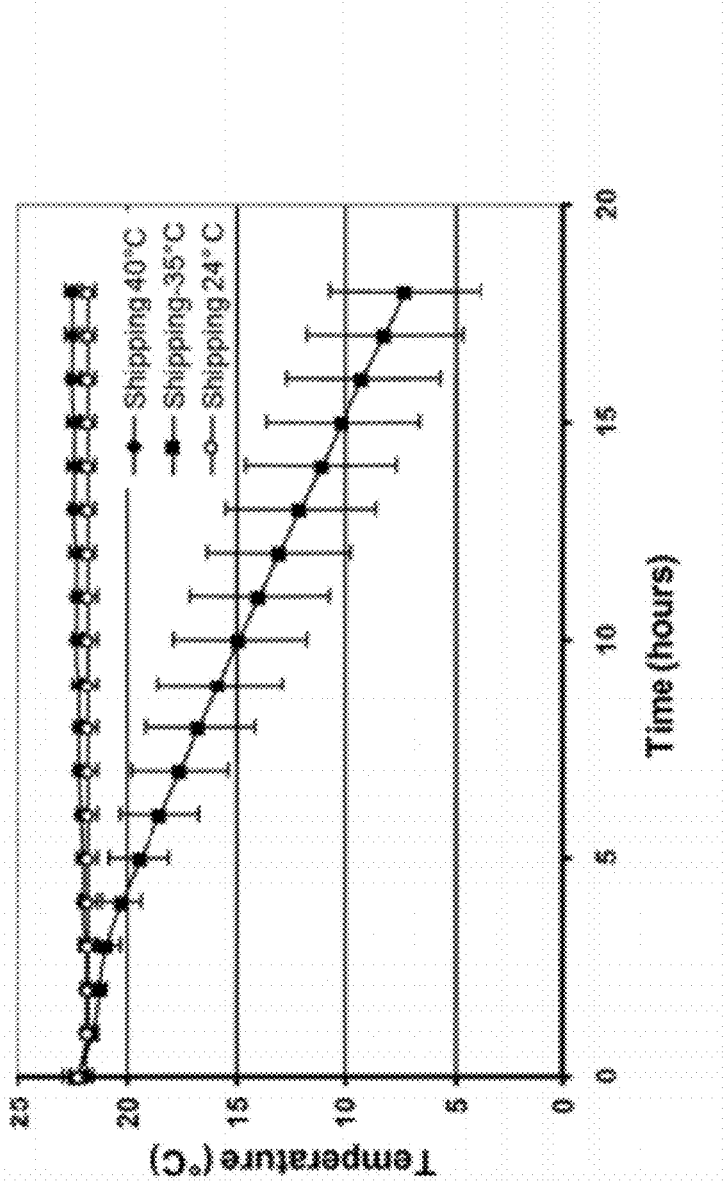
Fig. 9 – Temperature Profiles of Preferred Embodiment in Insulated Boxes

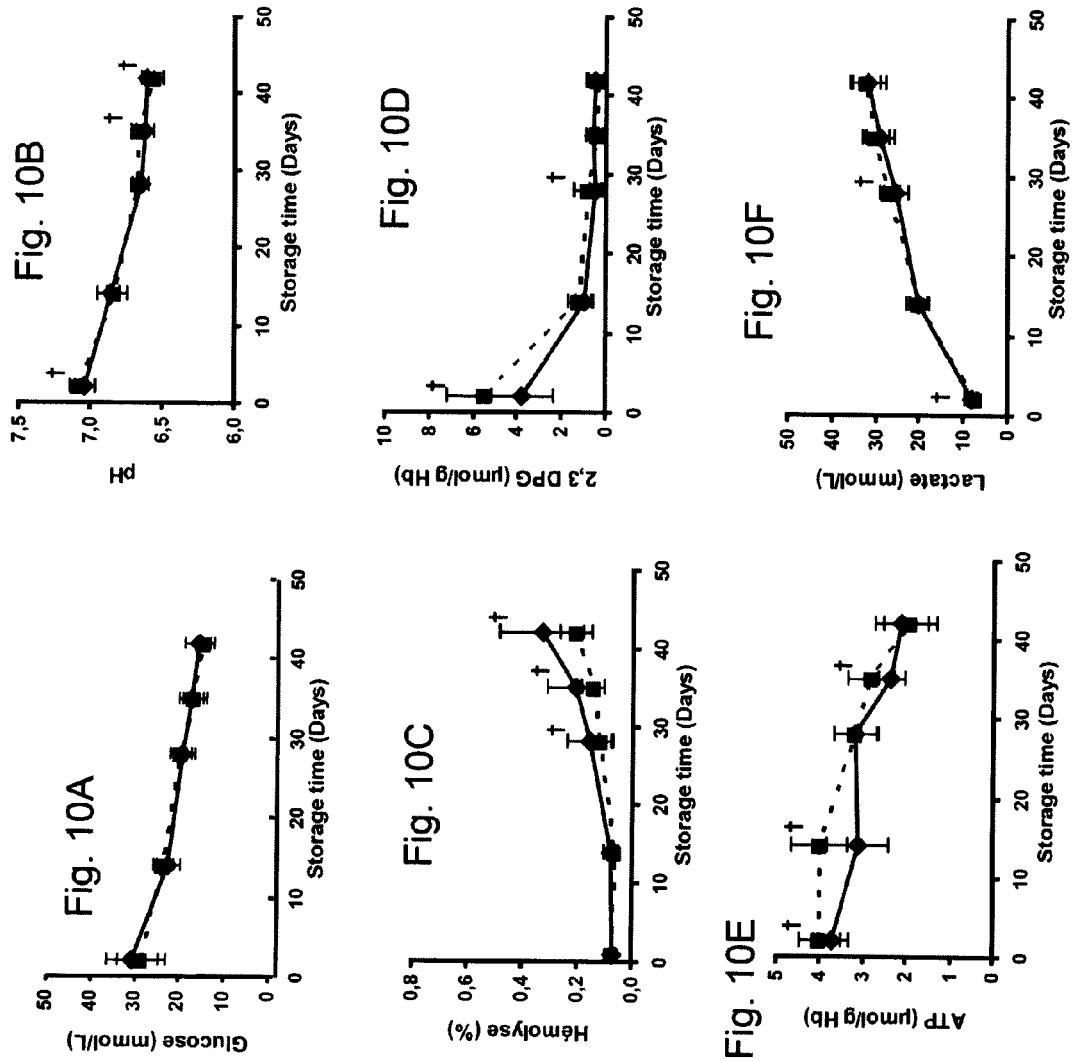
Comparison of Hemolysis (Fig. 10A), pH (Fig. 10B), ATP (Fig. 10C), 2,3-DPG (Fig. 10D), Glucose (Fig. 10E) and Lactate Levels (Fig. 10F) on Red Cell Concentrates Prepared from Blood Cooled to 22 ± 2°C Using Either Compocool II or the Preferred Embodiment (n = 24)

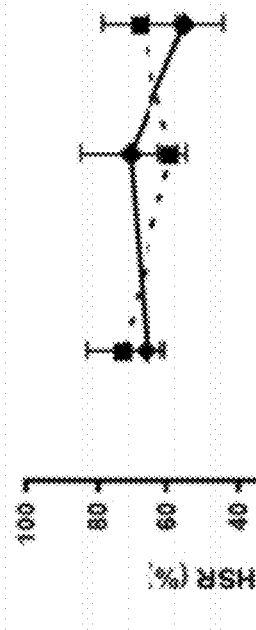
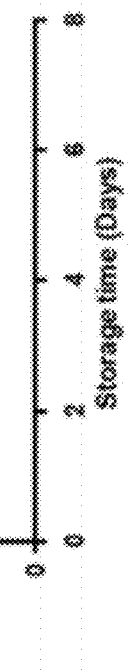
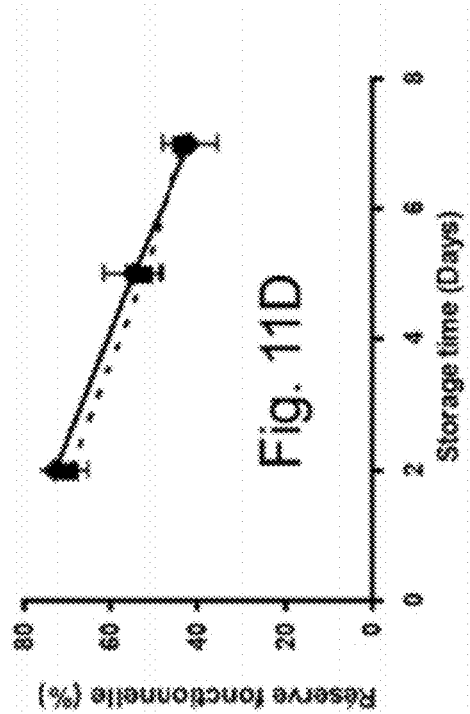
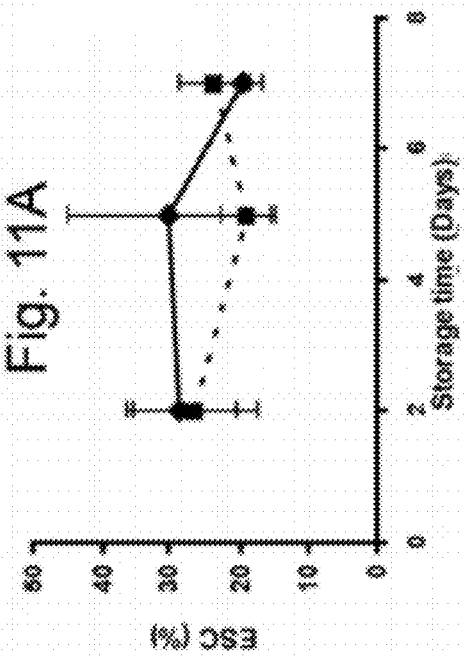
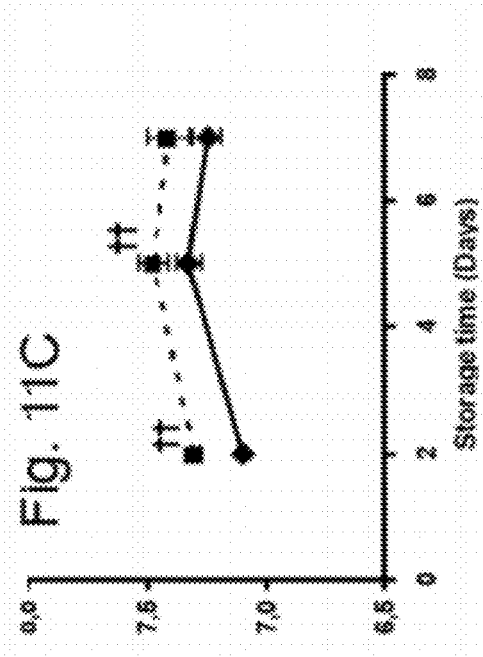

FABRICATING A FLEXIBLE RAPID BLOOD COOLING SYSTEM

RELATED APPLICATIONS

This application claims priority to U.S. Provisional Application No. 61/477,796, filed Apr. 21, 2011.

FIELD OF THE INVENTION

The invention relates to the field of blood cooling and storage for transport and processing.

BACKGROUND

Under existing standards, one can store whole blood for processing (to produce platelets and other blood products) for up to 24 hours at room temperature, provided the blood is rapidly cooled to 22±2° C. After collecting blood in blood bags, this rapid cooling is conventionally performed using cooling plates filled with butane-1,4-diol—a gel that melts at a temperature of 20° C. In gel phase, butane-1,4-diol absorbs heat from freshly collected blood. When the gel temperature reaches its phase change (melting) temperature, butane-1,4-diol can then absorb a lot of heat while maintaining a constant temperature of 18° C. This phase change material accumulates heat until it turns into a liquid. Afterwards, when brought back to a cooler ambient temperature, butane-1,4-diol returns to a solid gel state and releases stored heat.

By absorbing heat from blood, butane-1,4-diol allows rapid cooling (within 2 hours) of blood bags from 37° C. to 22±2° C. and maintenance of a constant temperature afterwards. Rapid cooling of blood bags ensures adequate blood product quality before component preparation. Butane-1,4-diol cooling plates were commercially introduced by NPBI in the early 1990's, following the work of Pietersz et al., "Storage of whole blood for up to 24 hours at ambient temperature prior to component preparation," Vox Sang 1989; 56(3): 145-50. Currently, Fresenius HemoCare (Redmond, Wash., USA) offers two cooling and transport systems for blood bags: Compocool, and a more recent version, Compocool II™/Compocool WB™, in which the butane-1,4-diol cooling unit is placed in an insulated crate. Additionally, Sebra/Haemonetics (Tucson, Ariz., USA) offers butane-1,4-diol-filled transparent pouches (ThermaSure), developed for the transport of platelet concentrates and blood units at 22±2° C.

The use of cooling plates containing butane-1,4-diol presents logistics issues for blood collection at remote sites. These cooling plates must be conditioned for at least 9 hours at a temperature of 4±2° C. before transport to the collection site. After conditioning, plates must be brought to 14-11.6° C. to prevent deleterious effects on the blood; this pre-warming step can take up to 60 minutes. Furthermore, since the heat-absorbing capacity of butane-1,4 diol declines in ambient temperatures that exceed 18° C., the performance of the plates gradually decreases in parallel with time of storage at ambient temperature. Additionally, ambient temperatures for the plates (i.e., during transport to the blood processing site) should ideally be in the 10-30° C. range. At an ambient temperature of −35° C., it has been shown that the Compocool II system is unable to maintain the desired temperature of blood bags for more than 2 hours. Thus, at such temperature extremes, blood bags must be transported in temperature-controlled units, as temperatures less than 20° C. are deleterious to platelet yield and quality—where platelets are produced from the blood.

Finally, butane-1,4-diol has to be periodically replaced, because it absorbs humidity over time, which alters its melting temperature and heat-absorbing characteristics.

Thus, a new system for rapid cooling and maintenance of freshly donated blood which avoids the disadvantages of butane-1,4-diol systems, and which can be readily fabricated, is needed.

SUMMARY

A blood-unit cooling system was designed to cool blood rapidly to about 22° C. and maintain it at about that temperature, even in ambient temperature extremes, for several hours. The system employs a preferred eutectic solution including 98% 1-dodecanol, 1.5% myristyl alcohol and 0.5% 1-decanol (melting point of 23° C.) contained in a sealed flexible polymer layer, to cool whole blood-filled bags. The preferred design used double-layered transparent polyethylene, with two sealed compartments filled with the solution, separated by a flattened and sealed portion between them. One of the two sealed compartments contacts one side of the blood bag and the other compartment is folded over to contact the other side of the blood bag. The transparent compartments allows an operator to verify at any time whether the solution is in a solid state, and the flexibility of the compartments eases the proper positioning of them around a blood bag. If the gel becomes deformed during use, it can be melted at about room temperature (e.g., 24° C.) and re-shaped.

The compartments are preferably relatively flat and thin, even when filled with the eutectic solution. This compact design reduces transportation costs and allows one to fit several of them, folded around blood bags, into one insulated transport box for shipment.

The system can be formed by forming inner compartments, by laying two polymer sheets, one on the other, and sealing them on three sides, e.g., with a heat seal. The eutectic solution is then placed between the sheets through their open ends, preferably after melting it first. To form one finished product, at least two finished inner compartments, with eutectic solution in each, are needed.

Outer compartments are then formed using a second set of two polymer sheets are sealed in a middle section to separate two compartments, and then sealed on all sides except the ends of each compartment. The finished inner compartments are placed through the open ends, and the ends are then sealed.

Each compartment is preferably about the same length and width dimension as a blood bag, so that both sides of the major surfaces of a blood bag are covered when the compartments are folded over a sandwiched blood bag. The compartments are preferably formed from polyethylene sheets. Other connections which are sufficiently flexible to allow the compartments to fold over each other are also suitable.

The cooling system allows conditioning of the compartments at room temperature (22° C. or less) for about 12 hours, and can reduce the temperature of blood in bags to 22±2° C. in about 2 hours. The temperature of the blood in the bags can be maintained for several hours, when the system with blood bags is placed in an insulated transport box, even in extremes of temperature.

BRIEF DESCRIPTION OF THE DRAWINGS

FIG. 1 shows a plan view of the preferred dual-compartment containment of the eutectic solution.

FIG. 2 shows a sectional view of the preferred dual-compartment device of FIG. 1, showing the inner and outer compartments.

FIG. 4A compares the gelling kinetics of butane-1,4-diol with the preferred embodiment.

FIG. 4B compares the melting kinetics of butane-1,4-diol with the preferred embodiment. Gelling thermal profiles in FIGS. 4A and 4B were measured at 4±2° C. after equilibrating phase change materials at 37±2° C. Melting thermal profiles were measured at 37±2° C. after equilibrating phase change materials at 4±2° C. Means±standard deviations from 3 experiments.

FIG. 5 shows the kinetics of cooling to 22±2° C. of 25% glycerol bags pre-equilibrated at 37±2° C. using the preferred embodiment, compared with another differently designed embodiment with the same eutectic solution. Six pouches filled with 25% glycerol equilibrated at a temperature of 37±2° C. were treated and packaged with Preferred Embodiment or the other invention embodiment (Phase 22 Rev-C) using the same eutectic solution. Boxes containing packaged materials were stored at room temperature. Means±standard deviations from 3 boxes of 6 pouches each (n=18 pouches).

FIG. 8 shows the influence of the number of gelling/melting cycles undergone by the preferred embodiment on the capacity (as measured by cooling time to the desired temperature) to cool 25% glycerol bags to 22±2° C. (n=4).

FIG. 9 shows temperature profiles of the preferred embodiment stored in commercial insulated (VIP™) boxes without any blood collection set, and exposed to extremes of temperature. This experiment was performed to model transport of the preferred embodiment from a blood processing center to a remote collection site where a blood drive is to be held. Insulated boxes were loaded with 16 Preferred Embodiments pre-conditioned at 20±2° C. After closing, boxes were stored in extreme conditions (24° C., +39° C., or −35° C.). Five thermal probes strategically positioned within each box were used for temperature recording for 18 hours. Temperatures indicated are means±standard deviations from 3 independent experiments.

FIGS. 10A, 10B, 10C, 10D, 10E and 10F respectively show a comparison of hemolysis, pH, ATP, 2,3-DPG, glucose and lactate levels in red cell concentrates prepared from blood cooled to 22±2° C. using either Compocool II™ or the preferred embodiment (n=24). Dashed lines ( - - - ) represent means±standard deviations of measurements on blood products prepared from whole blood cooled to 22±2° C. with Compocool II; full lines (-) are measurements from blood cooled with the Preferred Embodiment. SAG-M red cell concentrates were prepared with the Atreus system (Caridian-BCT).
[†]Indicates a statistically significant difference (p<0.05) between the 2 cooling systems.

FIGS. 11A, 11B, 11C and 11D respectively show a comparison of ESC, HSR, pH and functional capacity assays of platelets, from platelet concentrates prepared from blood cooled to 22±2° C. using either Compocool II™ or the preferred embodiment (n=3). Dashed lines ( - - - ) represent means±standard deviations of measurements on blood products prepared from whole blood cooled to 22±2° C. with Compocool II; full lines (-) are measurements from blood cooled with the Preferred Embodiment, [††]Indicates a statistically significant difference (p<0.05) between the two cooling systems.

DETAILED DESCRIPTION

Figure 3:
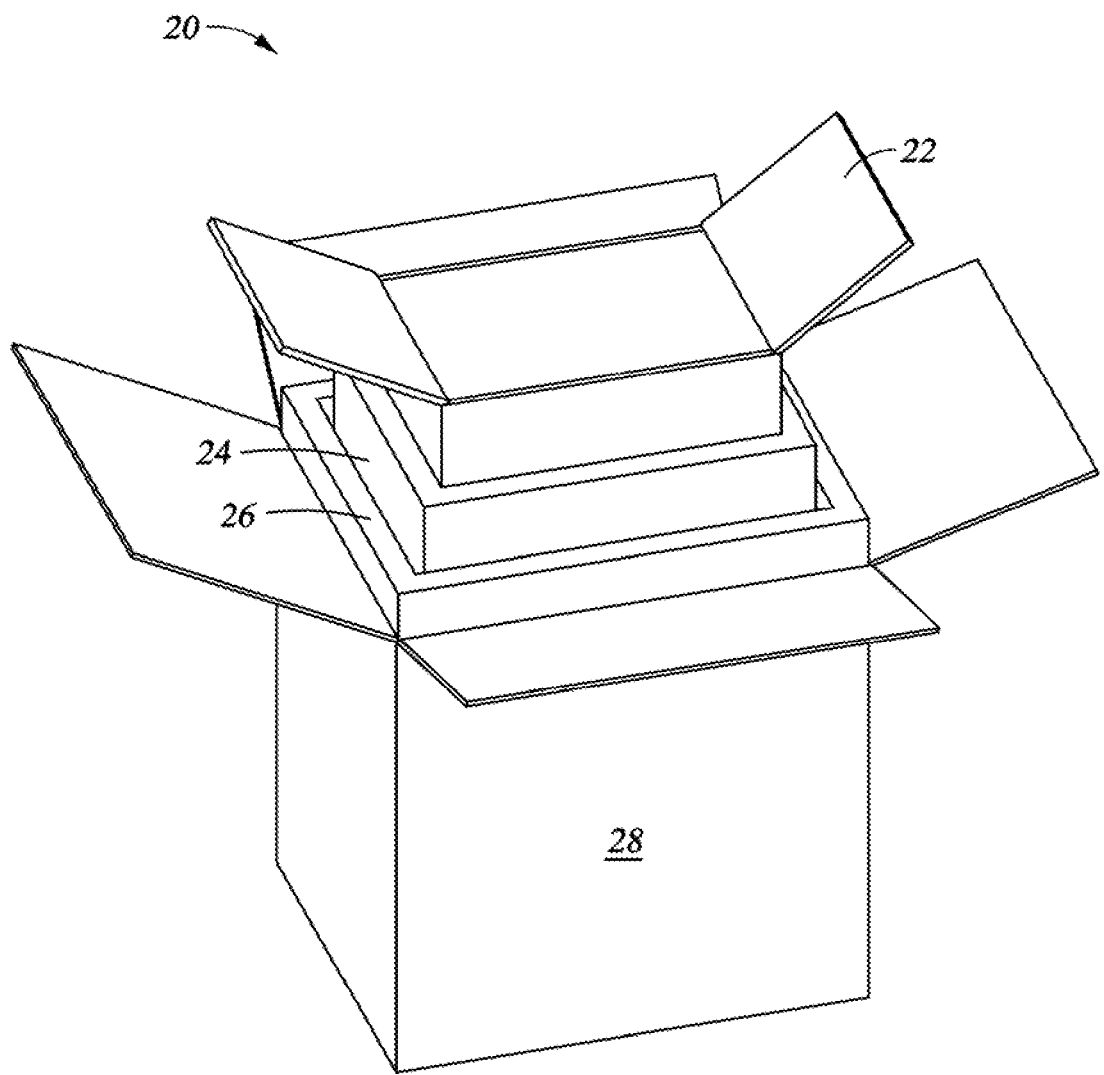
FIG. 3 shows a preferred insulated transport box VIP™ (made by TCP Reliable, Inc., Edison, N.J.) for the dual-compartment device of FIG. 1 while sandwiching a blood bag.

FIG. 1 shows a preferred embodiment 10 of the transparent, dual-compartment containment of the preferred eutectic solution, wherein the outer compartment has a first compartment 12 separated from a second compartment 14 by a flexible intermediate portion 16 (which is preferably a flattened, sealed section of double-layered polyethylene). Each of the outer compartments 12 and 14 includes within it an inner compartment, 12A and 14A, respectively, as shown in FIG. 2. Inner compartments 12A and 14A contain the eutectic solution, and are contained in the outer compartments for an additional barrier against leakage. Other designs and layering of compartments are readily apparent and within the scope of the invention, including additional outer compartments layered over the inner compartment, or elimination of the inner compartments and loading of the eutectic solution directly into the outer compartments 12 and 14. Different methods of flexibly joining the outer compartments are also possible, including attaching outer compartments with flexible fasteners made of rubber or a material which can be bent to hold the compartment in a desired configuration and then hold the compartments in that position, e.g., wire.

In operation, a blood bag is placed on first compartment 12 and second compartment 14 is folded over the blood bag. Several blood bags can be placed, side-by-side to conserve space, into an insulated transport box 20 (VIP™ made by TCP Reliable, Inc., Edison, N.J.) shown in FIG. 3.

The preferred embodiment 10 (with inner and outer compartments each made of polyethylene) was tested for durability by dropping from a height of 120 cm, which is typical of the height of a counter. No leaks or breaks of the wrapping were observed in this test.

A number of other containers for the eutectic solution can be used in place of preferred embodiment 10, provided they can maintain the eutectic solution in contact with a blood bag and provide sufficient heat transfer to rapidly cool the blood to about 22° C., and then maintain it at that temperature for a sufficient period to allow transport and processing of blood products. A number of other polymers or materials other than polyethylene would be suitable for forming the containers. Suitable containers for the preferred eutectic solution which can effectively cool the blood bag, to 22±2° C. and maintain that temperature for a sufficient period to allow blood processing, include containers formed like bags to cover the entire surface of a blood bag, or separated layers of containers, such that blood bags can be placed between them.

Several embodiments for containers were designed and compared, as shown in Table I below.

TABLE I

Comparison of Phase 22 Prototypes Rev-A, Rev-B and Rev-C with Compocool II

|  | Prototype Phase 22 Rev-A | Prototype Phase 22 Rev-B | Prototype Phase 22 Rev-C | Compocool II |
|---|---|---|---|---|
| Cooling Unit | | | | |
|  | Unitary pouch design of dimensions below | Design as shown in FIG. 1 | Unitary pouch design of dimensions below | Unitary cassette design |
| Dimensions/Cooling Unit (cm) | 16.5 × 11.5 × 2.0 | 16.5 × 11.5 × 2.0 | 23.5 × 16.5 × 2.0 | 30.6 × 16.5 × 4.5 |
| Eutectic Solution | Mixture 98% 1-dodecanol, 1.5% myristyl alcohol, 0.5% 1-decanol | | | Butane-1,4-diol |
| Melting Point | 23° C. | | | 20° C. |
| Weight/Cooling Unit (kg) | 0.4 | 0.4 | 0.7 | 2.5 |
| Conditioning | >12 hours at 20 ± 2° C. | >12 hours at 20 ± 2° C. | >12 hours at 20 ± 2° C. | >9 hours at 4 ± 2° C. |
| Insulated Box | | | | |
|  | As shown in FIG. 2 | | | Insulated EPS box |
| External Dimensions (cm) | 40 × 40 × 40 | | | 39 × 32 × 30 |
| Thermal Insulation | 2.5-cm thick vacuum panels (R-30*) 4-cm thick expanded polystyrene (R-4*) | | | 2.5 cm expanded polystyrene (R-3.8*) |
| Containment capacity (of 450 to 500 mL blood bags) | 1 to 6 | | | 1 to 6 |

*"R" is a measure of thermal resistance.

There are also a number of variations of the preferred eutectic solution,—including 1-dodecanol and other ingredients or proportions than those shown above, which do not change the essential characteristics of the eutectic solution—which are within the scope of the invention. The only limitation on variations of the eutectic solution is that it must allow rapid cooling of blood to about 22° C.—should also have the other desirable characteristics of the preferred eutectic solution, such as maintenance of blood temperature in temperature extremes.

Insulated transport box 20 has a corrugated outer layer, an expanded polystyrene layer 24 inside the corrugated outer layer 22, and an innermost layer of vacuum panels 26. Other insulated boxes using different designs can be substituted for transport box 20, and are within the scope of equivalents of the invention. Box 20 allows several of the preferred embodiments 10 covering blood bags to be arranged side-by-side, thus conserving space and also enhancing temperature maintenance from the effect of having several of the preferred embodiments (with phase change material for each) in each box. Other stacking arrangements for preferred embodiment 10 and blood bags can be used including stacking one on top of another. One can also have only one preferred embodiment 10 per box, or more, as desired.

Where storage is for short periods, or for storage at near 22° C., it may not be necessary to use an insulated transport box.

Re-Usable

The preferred embodiment is re-usable. To test the efficacy of the preferred eutectic solution to cool blood bags to 22±2° C. after several conditioning cycles, preferred embodiments were subjected to cycles of 24-hour storage at 4±2° C. (solid gel) and 37±2° C. (liquid). Before assays, preferred embodiments were conditioned and used for cooling 4 bags filled with an aqueous solution of 25% glycerol. The temperature of bags was recorded to determine the time required to bring the temperature of the 25% glycerol solution from 37±2° C. to 24° C. Afterwards, preferred embodiments were successively incubated at 4±2° C. and 37±2° C. After 0, 12, 25, 50 and 75 such cycles, preferred embodiments were conditioned at 20±2° C. and used for cooling 25% glycerol bags. The time required to bring the temperature of the 25% glycerol solution to 24° C. was measured as a function of the gelling/melting cycle.

Even after applying 75 cycles of gelling/melting, no significant differences in the performance of the preferred embodiment were observed (FIG. 8). No leaks or wear of the polyethylene wrapping were noted.

Addition of a Protection Bag

To avoid contacting blood bags with a damaged, leaking package, the impact of adding a supplementary protection bag on the performance of the preferred embodiment was evaluated. The time required to cool 25% glycerol bags prewarmed to 37° C. was the same, whether the preferred embodiment was wrapped in a polyethylene protection bag (1.7±0.2 hours) or not (1.8±0.2 hours) (p>0.05). Accordingly, addition of one or more additional layers for protection of the preferred embodiment is within the scope of the invention.

Kinetics of Melting and Gelling

The preferred eutectic solution is 98% 1-dodecanol, 1.5% myristyl alcohol and 0.5% 1-decanol. However, other eutectic solutions which provide for rapid cooling of blood and maintenance at about 22° C. could be substituted.

FIGS. 4A and 4B compare the kinetics of melting and gelling of butane-1,4-diol and the preferred eutectic solution. These two phase change materials have slightly different gelling kinetics. Butane-1,4-diol gels at a temperature of 19-20° C. after a super-cooling step (FIG. 4A). Super-cooling corresponds to a phase during which the liquid state is maintained while butane-1,4-diol temperature is below its gelling temperature. Gelling of the preferred eutectic solution occurs at 22-23° C. The kinetics is faster than with butane-1,4-diol and super-cooling is much less pronounced, owing to the composition of the solution (FIG. 4A). However, the kinetics of melting of the two compositions are comparable (FIG. 4B).

Figure 7:
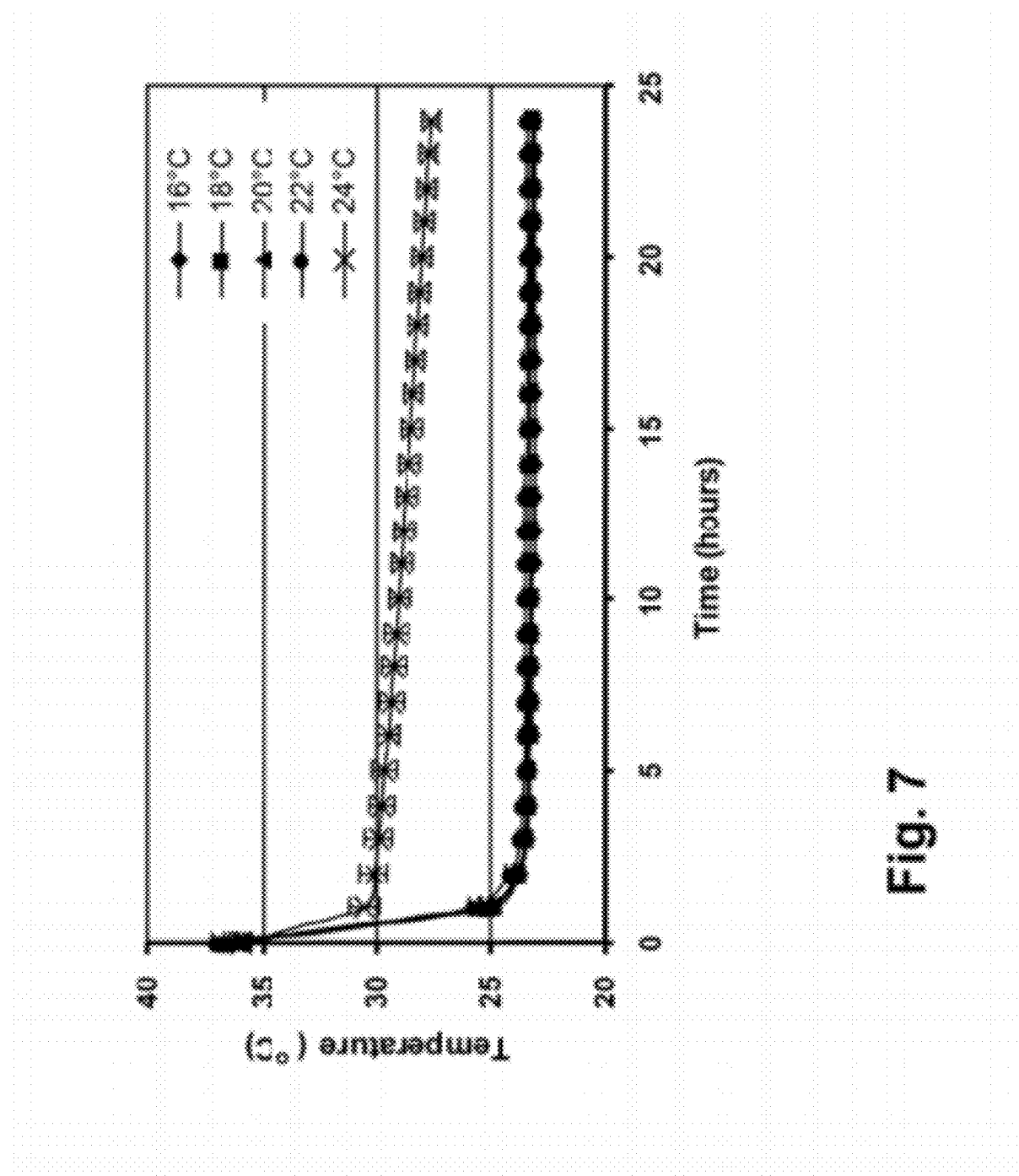
FIG. 7 shows temperature profiles of 25% glycerol bags pre-equilibrated at 37° C. and packaged with the preferred embodiment that has been pre-conditioned at 16° C., 18° C., 20° C., 22° C. or 24° C.

Conditioning and Performance of the Preferred Embodiment at Temperatures within the 16° C. to 24° C. Range Phase change materials are generally conditioned at a temperature that is at least 5° C. to 10° C. lower than their melting temperature. FIG. 7 compares temperature profiles of 18 bags filled with 25% glycerol during cooling to 22±2° C. using the preferred embodiment pre-conditioned at 16° C., 18° C., 20° C., 22° C. and 24° C. At 24° C., the preferred eutectic solution is in the liquid state, and is unable to cool glycerol solution to 22±2° C. When conditioned at 22° C., the preferred embodiment was able to reduce the temperature of glycerol bags to 22±2° C. in 1.7±0.2 hours. The preferred embodiment conditioned at 16° C., 18° C. and 20° C. was slightly more efficient, with cooling times of 1.2±0.1 hours, 1.4±0.1 hours, and 1.3±0.2 hours, respectively (p<0.05). It appears that the preferred embodiment can be conditioned between 18° C. and 22° C. (near room temperature) and still provide optimal performance.

Blood Products Including Platelet Production with the Preferred Embodiment

Table II below shows a comparison of blood products from blood cooled with the preferred embodiment and with Compocool II™. When using the preferred embodiment, blood bags were inserted between the two compartments (12 and 14 of FIG. 1) to ensure adequate contact with the contents of the bag, then inserted in a protective polymer bag, then placed vertically and side-by-side in an insulated VIP™ box. This arrangement allows simultaneous cooling and transport of up to 6 blood bags.

The Compocool II™ system was used according to the manufacturer's instructions. Before use, the butane-1,4-diol cooling unit was conditioned at a temperature of 4±2° C. for at least 9 hours. Immediately before use, preconditioned cooling units were left at room temperature until their temperature reach 14° C. to 16° C. One Compocool II case can hold up to 6 blood bags.

The blood products were prepared, following cooling and storage, using the Atreus Whole Blood Processing System for whole blood, and the OrbiSac System for preparing platelet concentrates from buffy coats (where the whole blood used in preparing the buff coats was cooled with either the preferred embodiment or with Compocool II™). Briefly 450 mL of blood was collected in Atreus collection sets containing 63 mL CPD with Sebra 1040 shakers (Sebra, Tucson, Ariz., USA). For these trials, shakers were used in volume mode, and the entire Atreus collection set was laid onto the tray. Within 30 minutes after phlebotomy, blood bags were cooled to 22±2° C. using either preferred embodiment or Compocool II. Each experimental arm included 24 blood donors. Blood was stored for 14 to 24 hours before processing into blood products with the Atreus system (2 C+overnight protocol and Orbisac). After processing, blood products were stored under conventional storage conditions.

Red cell concentrate samples were aseptically collected on storage days 2, 14, 28, 35, and 42 for in vitro assays. For platelet pools, in vitro parameters were measured on days 2, 5 and 7. The analysis of plasma units were done after at least 30 days of storage. Buffy coats were analyzed on day 2.

TABLE II

Comparison of the In Vitro Parameters of Blood Products Prepared with Atreus and OrbiSac from Whole Blood Cooled to 22 ± 2° C. with Compocool II ™ and the Preferred Embodiment

| | Cooling System | |
|---|---|---|
| Blood Products | Compocool II ™ | Preferred Embodiment |
| Whole Blood | | |
| Number of units | 24 | 24 |
| Storage time, hours | 17.7 ± 1.8 | 18.1 ± 2.7 |
| Temperature before processing, ° C. | 20.3 ± 0.3 | 23.0 ± 0.2* |
| Volume, mL | 456 ± 9 | 458 ± 11 |
| Red Cell Concentrates | | |
| Number of units | 24 | 24 |
| Filtration time, minutes | 0:26 ± 0:05 | 0:29 ± 0:06 |
| Percent recovery after filtration | 97 ± 1 | 97 ± 0 |
| Volume, mL | 260 ± 18 | 264 ± 20 |
| Hematocrit, l/l | 0.57 ± 0.03 | 0.56 ± 0.03 |
| Residual volume of plasma, mL | 14.3 ± 4.8 | 13.9 ± 3.6 |
| Hemoglobin, g/unit | 49.9 ± 5.3 | 50.1 ± 6.6 |
| Residual leukocytes, × $10^6$/unit | 0.41 ± 0.32 | 0.45 ± 0.44 |
| No. units >1 × $10^6$/unit | 1 | 2 |
| No. units >5 × $10^6$/unit | 0 | 0 |
| Percent hemolysis (Day 2) | 0.07 ± 0.01 | 0.07 ± 0.01 |
| Percent hemolysis (Day 42) | 0.21 ± 0.06 | 0.33 ± 0.15* |
| Buffy Coats | | |
| Number | 9 | 9 |
| Volume, mL | 52 ± 2 | 52 ± 4 |
| Hematocrit, L/L | 0.38 ± 0.08 | 0.40 ± 0.06 |
| Hemoglobin, g/unit | 6.3 ± 1.4 | 6.8 ± 0.7 |
| Platelet count, × $10^{11}$/unit | 0.86 ± 0.26 | 1.06 ± 0.29 |
| Platelet Concentrates (pool of 5 buffy coats) | | |
| Number | 3 | 3 |
| Volume, mL | 356 ± 21 | 338 ± 6 |
| Platelet count, × $10^{11}$/unit | 3.69 ± 0.56 | 4.18 ± 0.13 |
| Percent platelet recovery† | 76 ± 3 | 88 ± 3* |
| Residual leukocytes, × $10^6$/unit | 0.34 ± 0.00 | 0.46 ± 0.20 |
| pH (Day 5) | 7.48 ± 0.07 | 7.33 ± 0.05* |
| Plasma Units | | |
| Number | 24 | 24 |
| Volume, mL | 266 ± 16 | 265 ± 19 |
| Residual leukocytes, × $10^6$/unit | 0.27 ± 0.03 | 0.26 ± 0.02 |
| Fibrinogen (mg/dl) | 366 ± 145 | 355 ± 81 |
| Factor VIII (IU/mL) | 1.43 ± 1.98 | 0.89 ± 0.37 |
| Factor V (IU/mL) | 0.98 ± 0.12 | 0.94 ± 0.13 |
| vWF factor (IU/mL) | 1.10 ± 0.40 | 1.02 ± 0.35 |
| Sodium (mmol/L) | 171 ± 2 | 172 ± 2 |
| Potassium (mmol/L) | 3.72 ± 0.31 | 3.67 ± 0.34 |

*Indicates a statistically significant difference (p < 0.05) with Compocool II.
Mean ± standard deviation.
†Percent of platelet count measured in the Buffy coat pool before final preparation of the platelet concentrate.

The temperature of blood bags during storage was higher, on average by 2.7° C., with the preferred embodiment compared to Compocool II™ (p<0.05). There were no differences in blood bag volume nor in storage time before processing between the two arms of the study. Similarly, there were no differences in red cell concentrates prepared from blood cooled with Compocool II™ and the preferred embodiment in terms of filtration time, percent recovery post-filtration, residual leukocyte counts, residual plasma, and hemoglobin (Table II). However, the fact that blood bags cooled with the preferred embodiment were stored at a temperature that was on average 2.7° C. higher than bags cooled with Compocool II™ might have caused slight, yet statistically significant, differences in terms of hemolysis (day 42), ATP and 2,3-DPG content (FIGS. 10A, 10C, 10D). Although percent hemolysis at the beginning of storage were comparable, this parameter increased more rapidly after 4 weeks of storage in products prepared from blood cooled with the preferred embodiment. The percentage of hemolysis was still below 0.8% in all red cell concentrates. This parameter varied between 0.14% and 0.63% in red cell concentrates prepared from blood cooled with the preferred embodiment, and between 0.11 and 0.31% in red cell concentrates prepared from blood cooled with Compocool II™.

Furthermore, during storage, ATP (FIG. 10C) and 2.3-DPG (FIG. 10D) content of red cell concentrates prepared from blood processed with Compocool II™ were slightly higher than values in concentrates prepared from blood processed with the preferred embodiment.

Nine buffy coats were analyzed in the course of this study. The majority of these buffy coats were processed into platelet concentrates. Independently of the whole blood cooling system used the hi vitro parameters measured in buffy coats were comparable for both arms of the study (Table II).

Platelet recovery with OrbiSac was slightly higher with buffy coats prepared from whole blood cooled with the preferred embodiment. Although not statistically significant, platelet yields were higher when prepared from blood cooled with the preferred embodiment. This difference was paralleled with slightly lower pH values in platelet pools prepared from blood cooled with the preferred embodiment (FIG. 11C).

Comparison of coagulation factor, fibrinogen and electrolyte sodium and potassium) concentrations in plasma did not indicate any significant differences in units prepared from whole blood cooled with Compocool II™ vs. whole blood cooled with the preferred embodiment (Table II).

In conclusion, cooling blood with the preferred embodiment and storage for a time period simulating using it in net day processing, indicates the resulting blood products produced are fully comparable to those produced following cooling with the existing commercial Compocool II™ system.

The protocol for determining the characteristics reported in Table I and FIGS. 10A-10F; 11A-11D is set forth immediately below.

Biochemical and Hematological Analyses (Table I: FIGS. 10A-10F; 11A-11D)

Blood component volumes were determined using a density of 1.06 g/mL for whole blood and buffy coats, 1.07 g/mL for red cell concentrates, and 1.03 g/mL for platelet pools and plasma units.

Complete blood counts were determined with a Coulter AcT™ 5diff AL hematology analyzer (Beckman Coulter Canada, Mississauga, ON, Canada). Residual leukocyte counts were determined using the LeucoCOUNT kit (Beckman Coulter Canada, Mississauga, ON, Canada) run on a flow cytometer (FACS Calibur, Becton Dickinson). All analyses had to be completed on the day of sampling. For red cell concentrates, the 24-hour delay after leukoreduction by filtration also had to be complied with.

Sterility testing was performed on platelet concentrates immediately after component preparation. A second sterility test was done on platelet and red cell concentrates at the expiration date. No bacterial contamination was detected at the expiration date.

The pH measurements (at 22° C.) were done with a pH-meter (Beckman Coulter) immediately after sampling. Plasma hemoglobin was measured with a HemoCue Plasma/Low HB photometer (HemoCue, Angelholm, Sweden) on samples that had been frozen at −80° C. Percent hemolysis was calculated according to the following equation: ([Free Hb]/[Total Hb]×(100−HCT). ATP, glucose, lactate and 2,3-DPG levels were determined using the following commercial kits: ATP determination kit (Perkin Elmer, cat. #6016947) for ATP; Method no 735 (Sigma-Aldrich, cat. #735-10, St. Louis, Mo.) for lactate; Ampex® Red Glucose/Glucose Oxidase Assay Kit (Molecular Probes, cat. #A-22189) for glucose; and the 2,3-DPG (2,3-diphosphoglycerate) kit (ROCHE Diagnostics, cat. #148334) for 2,3-DPG.

The evaluation of platelet activation was done by flow cytometry according to a conventional procedure. Briefly, platelet concentrates were diluted to a concentration of approximately $200 \times 10^6$ platelets/mL with autologous plasma. Platelets were fixed by adding an equal volume of 2% paraformaldehyde. After a 10-minute incubation, the suspension was diluted with 10 mM phosphate, pH 7.4, supplemented with 150 mM NaCl. Labeling was done by incubating an aliquot of 25 µl of the fixed suspension with 10 µL anti-CD62p (Immunotech Inc., Vaudreuil-Dorion, QC, Canada) and 10 µl anti-CD41 (Becton Dickinson). After 30 minutes of incubation, the suspension was diluted in 0.5 mL FACSFlow solution (Becton Dickinson). The analysis was performed on a FACScalibur flow cytometer with the Cell Quest software (BD Biosciences). Platelet functional capacity was evaluated by incubating 25 µL of the suspension with the GPAP peptide (Sigma) and human alpha-thrombin (Sigma) for 10 minutes at 37° C. Afterwards, platelets were fixed and immunologically labeled according to the procedure described above for CD62p activation. Hypotonic shock response (HSR) and extent of shape change (ESC) assays were done by aggregometry with the Aggrolink software (Whole Blood Lumi-Aggregometer, model #540VS, Chrono-Log Corporation, Havertown, Pa., USA), according to the protocol described by S. Holme et al (Holme S. Moroff G. Murphy S: A multi-laboratory evaluation of in vitro platelet assays: the tests for extent of shape change and response to hypotonic shock. Biomedical Excellence for Safer Transfusion Working Party of the International Society of Blood Transfusion. Transfusion 1998; 38(1): 31-40, incorporated by reference). Platelet count in samples was adjusted to $200 \times 10^6$ platelets/mL with plasma depleted of autologous platelets. Reaction pH was adjusted to 7.0 with 1 M HEPES buffer.

Cooling and Temperature Holding Profiles of Glycerol-Filled Bags with the Preferred Embodiment and Compocool For the trials depicted in FIGS. 5-9, collection bags from Atreus collection sets (CaridianBCT, Zaventem, Belgium) were filled with 450 mL 25% glycerol. This solution has a specific gravity of 1.060 g/mL, which is comparable to that of whole blood with a hematocrit of 45%.

A thermal probe coupled to a temperature recorder (Hobo, Onset, USA) was inserted in the center of each bag. Before testing, collection bags were equilibrated at 37±2° C. to simulate blood collection. Complete collection sets (collection bag, filters and satellite bags) were inserted in a protective polyethylene bag, then cooled and stored for up to 24 hours using the preferred embodiment (or another embodiment—labeled "Rev-C") or Compocool II. To simulate extreme temperature conditions, packages were stored in external environments conditioned at either 24° C., −35° C. or 39° C.

Figure 6A:
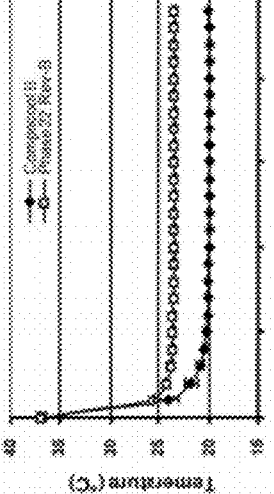
FIG. 6A shows temperature profiles of 25% glycerol bags initially equilibrated at 37° C. before cooling with: (i) preconditioned preferred embodiment or (ii) preconditioned Compocool when insulated boxes containing packaged materials are stored at 24° C.
Figure 6B:
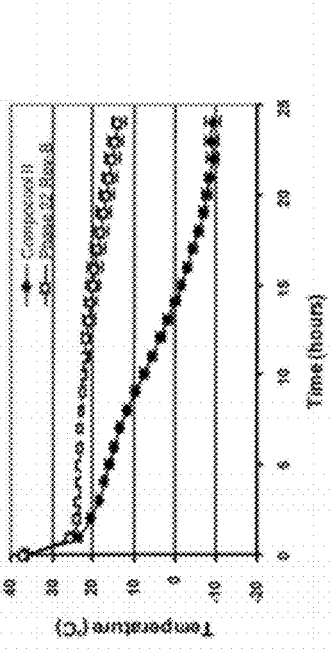
FIG. 6B shows temperature profiles of 25% glycerol bags initially equilibrated at 37° C. before cooling with: (i) preconditioned preferred embodiment or (ii) preconditioned Compocool when insulated boxes containing packaged materials are stored at −35° C.

FIG. 6 compares the temperature profiles of bags filled with 450 mL of an aqueous solution of 25% glycerol, cooled with the preferred embodiment and Compocool II™. At room temperature (24° C.), all glycerol bags reached a temperature of less than 24° C. in 17±0.2 hours with the preferred embodiment, compared to 0.9±0.2 hours with Compocool II™ (p<0.05) (FIG. 6A). The temperature of bags was maintained at 23.4±0.1° C. and at 20.0±0.1° C. with the preferred embodiment and Compocool II™, respectively (p<0.05).

Figure 6C:
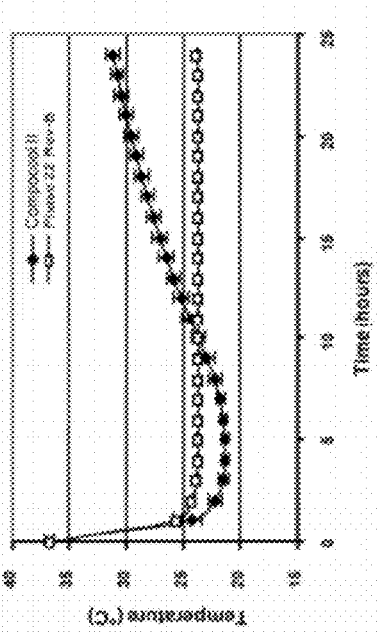
FIG. 6C shows temperature profiles of 25% glycerol bags initially equilibrated at 37° C. before cooling with: (i) preconditioned preferred embodiment or (ii) preconditioned Compocool II™, when insulated boxes containing packaged materials are stored at 39° C.

Extreme outdoor temperature conditions affected the temperature of the glycerol bags placed in insulated containers, simulating transport conditions. At −35° C., the temperature of the glycerol bags was maintained at 22±2° C. for 15.4±2.7 hours with the preferred embodiment, but only for 2.3±0.3 hours with Compocool II (p<0.05) (FIG. 6B), in an external temperature of +39° C., the temperature of glycerol bags stored in Compocool II gradually increased to exceed 24° C. after 11.0±0.9 hours, whereas the temperature of bags stored with the preferred embodiment was maintained at 22±2° C. for at least 24 hours (FIG. 6C). Thus, the preferred embodiment is able to maintain the temperature of blood solutions for a longer time in extreme temperature conditions, particularly in summer-season temperatures, compared to Compocool II™.

FIG. 9 compares the temperature of the preferred embodiment packaged in an insulated box (VIP™, made by TCP Reliable, Inc., Edison, N.J.) when subjected to extreme temperature conditions during, transport. The insulated box adequately maintains preferred embodiment conditioning when the outside temperature is 39° C. However, despite its very high thermal resistance (R value), the insulated box was able to maintain an adequate preferred embodiment temperature for only 4 hours when exposed to extreme winter temperatures (−35° C.). However, the maximum allowable time in these conditions could be shortened depending on the number of the preferred embodiments inside an insulated box—more blood units in a box, each packaged with a preferred embodiment, may tend to slow heat loss.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also noted that as used herein and in the appended claims, the singular forms "a," "an," and "the" include plural reference, and the plural include singular forms, unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A process for forming a flexible polymer pouch containing at least two inner containers which contain a phase change material consisting essentially of 98% 1-dodecanol, 1.5% myristyl alcohol and 0.5% 1-decanol, and preparing the pouch for rapid cooling of blood bags filled with freshly drawn blood, wherein the pouch will be covering a major portion of each of the two largest surfaces of the blood bags for about 2 hours for the temperature of the blood in the blood bags to drop to 22° C.±2° C., the process comprising the steps of:
    forming said at least two inner containers for the phase change material using at least two overlaying polymer sheets wherein a seal at their edges is completed after the phase change material is inserted;
    forming at least one outer container for the inner containers using at least two overlaying polymer sheets which are sealed along at least one axis to form two compartments;
    sealing at the edges of said compartments after the inner containers are inserted into said compartments, to form the flexible polymer pouch; and
    preconditioning the flexible polymer pouch at about 22° C.

2. The process of claim 1 wherein the polymer sheets are made of polyethylene.

3. The process of claim 1 wherein the polymer sheets are transparent.

4. The process of claim 1 wherein a portion of the edges of the polymer sheets forming the inner containers are sealed before the phase change material is inserted.

5. The process of claim 1 wherein a portion of the edges of the polymer sheets forming the outer compartments are sealed before the inner containers are inserted.

6. The process of claim 1 wherein additional inner containers are formed and used to contain the inner containers containing the phase change material.

7. The process of claim 1 further including preconditioning the flexible polymer pouch at about 22° C. for about 12 hours.

8. The process of claim 1 wherein (the blood bags contain 450 ml of blood.

9. The process of claim 8 further including extracting platelets from the contained blood.

* * * * *